United States Patent [19]

Raskova et al.

[11] Patent Number: 4,975,450
[45] Date of Patent: Dec. 4, 1990

[54] ANTIDIARRHEAL

[75] Inventors: Helena Raskova, Prague; Viktor Bauer, Samorín; Zdenka Urbanova, Kutná Hora; Ludek Beneš, Bratislava; Svorad Stolc, Bratislava; Valéria Dittertová, Bratislava; Anna Babulová, Bratislava, all of Czechoslovakia

[73] Assignee: Slovenska Akademia Vied, Bratislava, Czechoslovakia

[21] Appl. No.: 247,135

[22] Filed: Sep. 21, 1988

[30] Foreign Application Priority Data

Sep. 21, 1987 [CS] Czechoslovakia ............... PV 6793

[51] Int. Cl.$^5$ ............................................. A61K 31/40
[52] U.S. Cl. ..................................... 514/428; 514/867
[58] Field of Search ................................ 514/428, 867

[56] References Cited

U.S. PATENT DOCUMENTS 4,647,562  3/1987  Davis ................................. 514/428
4,721,722  1/1988  Davis ................................. 514/428

FOREIGN PATENT DOCUMENTS 125666  6/1967  Czechoslovakia .
126102  7/1967  Czechoslovakia .

*Primary Examiner*—Frederick E. Waddell
*Attorney, Agent, or Firm*—Klein & Vibber

[57] ABSTRACT

The object of the invention is to provide a medicament for the therapy of diarrheal diseases, especially of non-specific character, which medicament is designed for oral application and contains, as active component, ($\pm$)-trans-2(1-pyrrolidinyl) cyclohexylester of 3-(n)-pentyloxycarbanilic acid, or a salt of said ester with a pharmaceutically acceptable acid, and, optionally a physiologically harmless vehicle. The active component has also other therapeutical effects such as antiulcerose, spasmolytic and locally anaesthetic ones.

4 Claims, No Drawings

ANTIDIARRHEAL

FIELD OF THE INVENTION

This invention relates to a substance for treating non-specific diarrhea types caused by, among other agents, enteropathogens and enterotoxins. Apart from its antidiarrheal effect, the active substance possesses significant antiulcerose, spasmolytic, locally anaesthetic and gastric cytoprotective effects.

Diarrhea and diarrheal diseases are one of the most frequent causes of morbidity and mortality especially in less developed countries, where the number of those killed by such diseases is estimated at about 5 million persons per annum. Particularly dangerous are diarrheal diseases of the new-born and the youngest group of babies (S. Hughes: Drugs 26, 80–90 (1983)).

In mechanized or automated large-capacity farms, diarrhea and infections of the respiratory tract are frequent, especially with young livestock, and the high mortality or growth deceleration thereof have a considerable negative economical effect. Diarrheal diseases of man and animals are caused by a plurality of etiological factors, especially of microbial and viral character. The most prevalent microbes are gram-negative bacteria, *Escherichia coli* and *Vibrio cholerae*.

For microorganisms to cause diarrhea, two factors must be present:

(a) Adherence factors in the form of specific fimbria (pili) which enable the microorganisms to adhere to epithelial cells of the small intestine is mucous membrane and to reproduce. When orally received, microorganisms get into the small intestine without being affected by gastric acid. After reproduction, these microorganisms settle in the colon.

(b) Some of gram-negative bacteria produce toxins which affect opithelial cells and raise the activity of adenylate cyclase and cyclic adenosine-5'-monophosphate (cAMP). A higher level of cAMP leads to a predominance of liquid flow from the tissues into the small intestine lumen. The loss of liquids and ions results in dehydration and acidosis, which may be life-threatening.

These conditions can be managed only sporadically, because of the difficulties of ascertaining a bacterial prophylaxis and in mastering the hygienic epidemiologic situation, or of an adequate rehydration therapy in practice.

DESCRIPTION OF THE PRIOR ART

Diarrheal diseases are treated by rehydration therapy using preparations composed of various salts (potassium chloride, sodium chloride, sodium hydrogen carbonate) and glucose whereby a quick compensation for the loss of water and ions as well as for acidosis occurs. However, the occurrence of diarrheal diseases is not influenced. Other substances of the same kind produce similar results.

In addition, there are anticholinergic substances applied together with spasmolytics such as Reasec$^R$ (Janssen) which contain diphenyloxylate and atropin. Both human and veterinary medicine, use chemotherapeutic agents with antibacterial effects, such as sulfonamides, or antibiotics, are availed of, which are apt to suppress certain infections.

Medicaments are also aimed at the sphere of regulation depending on receptors, especially those localized on the basolateral membrane, further by means of an intracellular mechanism of the intervention by the so-called secondary messenger, and by influencing the transport mechanism, especially boundary membranes. The modulation of receptor-dependent regulation mechanisms can be influenced, to some extent, by medicaments of the type alpha$_2$ adrenergic agonists such as clonidine (Catapresan$^R$) (E. B. Chang et al, Gastroenterology 91, pp.564–9 (1986)), somatostatin, or encephalin, and morphine analogs. For influencing the transport of ions through the membrane it is also possible to use alpha$_2$ adrenergic agonists (E. B. Chang et al, Am. J. Physiol. 1982, p.242). Reference has been also made to the use lidamidine, i.e. the medicament having a damping effect on the intestine peristaltics (M. D. Dharmsathphorn:Gastroenterology 91,769–775 (1986)).

Disadvantages of antidiarrheal medicaments, i.e. those referred to in professional papers rather than those medicaments of this type applied in practice, include their secondary strong effects such as antihypertensive effects (clonidin), growth factors (somatostatin) habituation and/or incomplete preclinical research (encephalin derivatives). The application of large doses of antibiotics and long administration thereof has not proved optimum in epidemical diarrhea localities. Where the diarrhea inducing agent is cholera toxin, however, there does not exist any efficient protection, except for inoculum which is not sufficiently patent, either, and gives short-term protection only (3 months) and low efficiency (30–40%).

SUMMARY OF THE INVENTION

Some disadvantages and drawbacks of prior art therapy as are eliminated by the antidiarrheal agent according to the present invention, whose active component is (±)-trans-2(1-pyrrolidinyl) cyclohexylester of 3-(n)-pentyloxycarbanilic acid of the formula

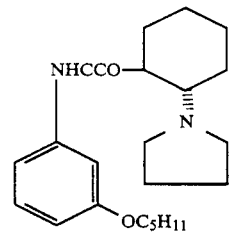

or salts of said ester with pharmaceutically acceptable acids the preferably, hydrochloride, adipate and fumarate salts, and optionally with a physiologically harmless vehicle in the form suitable for oral administration.

The process for preparing the active substance has been protected by Czechoslovakian patents, Nos. 125,666 and 126,102. At present, the medicament containing the active substance is known and has been patented as a therapeutic agent with antiulcerose, spasmolytic and locally anaesthetic effects, (see Czechoslovakian Authorship Certificate No. 237,705), from which its effect on the intestinal propulsion could not be deduced, and unexpected antidiarrheal effects have been observed in different experimental models with the present medicament.

The medicament exhibits the well-known locally anaesthetic effects (L. Benes et al, Arzeneim.-Forsch.1902 (1969)); locally anaesthetic and spasmolytic effects (P.Svec et al, Farm.Obzor 45, p.355 (1976)); the character of this effect, its initiation, development, duration and termination as well as maintenance of its locally anaesthetic activity even in media with decreased pH value at the acid side have been referred to by S. Stole et al (Brat.Lek.Listy 70, p.297 (1978)); antiulcerose effects with a marked gastric cytoprotective effect by V. Nosalova et al (New Pharmacology of Ulcer Disease, ed. M. Fisher, Prager Publ. London 1986, p.113); and further a significant reduction of adenylate cyclase activity (Hynie et al: Cs. Fysiol. 35, pp.338-339 (1986)), which is probably one of the possible mechanisms of antidiarrheal effects of the substance of the above formula. A low acute toxicity, subchronical and chronical toxicity together with the newly disclosed effects constitute excellent conditions for the therapy of diarrheal diseases. The elimination of the high dehydration of organism resulting from, among other causes, the actual diarrheal disease, is capable of reducing the mortality with groups of involved individuals.

The antidiarrheal medicament of the above formula, if administered in doses of 10 and 20 mg per diem for one to three days after birth to calves of average weight of 40 kg, has given a significant reduction of diarrhea with involved animals depending upon the dose applied. With the referenoe individuals (n=66) diarrhea has occurred with about 80% thereof. The medicament of the invention, if administered for 2 to 3 days in a 10 mg daily dose, reduced the diarrhea ocourrence by 40-50%, and with a 20 mg d aily dose during 3 days of administration even less than 4% (P<0.01). In the control group of calves to which no medicament was administered, a multiple mortality has been observed. Thus, for instance, control group of 66 calves to which no medicament was given has proved, if compared with the same number of calves treated with said medicament in capsule form containing 10 and 20 mg thereof, respectively, a statistically considerably higher number perish Similarly, the effect of the medicament of the above formula has been proved experimentally with mice whose diarrhea has been provoked by castor oil. The active substance in 20 mg dose per one kg, if administered 30 minutes before administering castor oil, has extended the latent period up to the beginning of the diarrhea from 91.2±4.4 minutes to 127.3±6.3 minutes. It also has been found that the active substance does not significantly influence the passage of intestine content (carbo adsorbens) either with mice or rats, unlike atropine. (Table 1).

TABLE 1 - Influence of pharmaceutical substances on the intestinal passage of carbo adsorbens (100% is the complete intestine length):

|  | mice | | rats |
| --- | --- | --- | --- |
|  | small intestine | complete intestine | small intestines |
| reference | 91.7 ± 2.2 | 75.0 ± 1.9 | 58.7 ± 2.5 |
| substance of the formula 20 mg/kg | 96.6 ± 0.95 | 80.3 ± 1.2 | 60.1 ± 1.5 |
| atropin 5 mg/kg |  | 51.4 ± 2.6 | 46.3 ± 2.5 |

When the active substance of the formula is applied in a dose of 10-20 mg/kg, the retention of stomach content is unchanged, while the retention of stomach content increases after the application of atropin.

The results suggest that the active substance according to the present invention influences the secretion processes rather than the intestine content passage.

The following table (Table 2) gives the values of acute toxicity of (±)- trans-2-(1-pyrrolidinyl) cyolohexylester of 3(n)-pentyloxycarbanilic acid of the above formula, expressed as $LD_{50}$ in mg/kg with various animal species (mice, rat, rabbit, guinea-pig):

TABLE 2 - Mean lethal doses of the substance of the invention

TABLE 2

| Mean lethal doses of the substance of the invention | | |
| --- | --- | --- |
| mode of administration | male | female |
| | mice | |
| i.v. | 10.3 | 10.3 |
| i.p. | 56.0 | 59.0 |
| s.c. | 122.0 | 128.0 |
| p.o. | 790 | 840 |
| | rat | |
| i.v. | 11.8 | 13.8 |
| i.p. | 70.0 | 75.0 |
| s.c. | 295.0 | 283.0 |
| p.o. | 1110 | 1030 |
| | rabbit | |
| i..v. | 2.92 | — |
| i.p. | 46.5 | — |
| | guinea pig | |
| i.v. | 7.8 | — |
| s.c. | 73.2 | — |

One month toxicity study of rats with p.o. doses of 0.1; 1; 10 mg/kg has not shown any influence on the behavior of animals, and neither hematological, biochemical and morphological indices or the animal weight have not been considerably influenced, except for the two highest concentrations of administered doses with which the increases in weight has been in some cases lower than average.

Chronic six months toxicity studies effected on dogs (beagle) of both sexes has not exhibited with doses of 2; 10; 30 mg/kg any extensive changes in the weight of dogs. No toxic effect in hematological, biochemical and morphological indices has been observed with the two lower doses, except for minor changes in the heart activity, and particularly by influencing the pulse conductivity and further by psychomotoric unrest. With the two highest doses, a decrease in weight, defective behavior and mortality have occurred. Within the dose range of up to 2 mg/kg of animal weight no proofs about any harmfulness of the substance in the six months period of p.o. administration with the entire group of tested dogs have been found.

During the teratological and embryotoxic experiments on mice with doses of 0.21; 2.1; 8.4; 21; 42; 84 mg/kg of animal weight, which corresponds to 0.025; 0.25; 1; 2.5; 5; 10 % $LD_{50}$, no changes in the amounts of fetal weight implantates, placenta and amniotio liquor were found. The oocurrence of skeletal abnormalities was the same as in the reference group to which no medicament was applied. It was only with the highest dose of 84 mg/kg that palate fissure of less than 10% of the fetuses was observed.

With the substance of the above formula, in doses of from $2.5 \times 10^{-5}$ to $2.5 \times 10^{-3}$ M/disc, no mutagenous effects in experiments of the detection of recessive lethal mutations with *Drosophila melanogaster* have been found. Further either qualitative or quantitative mutations in tests on *Salmonella typhimurium* and *Escherichia* coli as well as mutation changes in reparative tests effected on the same species have not been observed.

The present medicament i.e. hydrochloride (±)-trans-2(1-pyrrolidinyl) cyclohexylester of 3-(n)-pentyloxycarbanilic acid, can be prepared by dissolving the substance in water or aqueous solutions, or other liquids, half-liquid bases, or, optionally, in suitable solvents such as. for liquid forms, usual stabilizing admixtures (e.g. phosphate buffer, emulsifiers (sorbimacrogels), suspension or emulsion stabilizers (e.g. esters of cellulose, colloidal silicon dioxide, bentonite)), and for solid form, by adding the usual adjuvants such as starch, lactose, methylcellulose, dextrane, magnesium stearate, microcrystalline cellulose or the like. The presupposed and low dose of the medicament does not influence the base of medicament form, the deoomposition, disintegration or the like thereof.

The compound of the formula i.e., the active substance, is prepared according to the prior Czechoslovakian patent specification Nos. 125,666 and 126,102.

DETAILED DESCRIPTION OF THE PREFERRED EMBODIMENTS

The invention is further described with reference to a number of examples which are illustrative only, and which do not serve to limit the scope of the disclosure and the accompanying claims.

EXAMPLE 1

Antidiarrheal in capsule form:

A capsule (22 mm length, 8 mm dia.) was filled with a mixture that was prepared by combining 20 g of the substance with 60 g of lactose. One capsule contained 20 mg of the active substance.

Similarly, capsules were prepared with 10 mg doses of active substance in which an amount of the substance corresponding to said 10 mg dose was added to lactose. The capsules were filled with the mixture so that each capsule contained 10 mg of the active substance.

EXAMPLE 2

Antidiarrheal in tablet form:

10 g of active substance were mixed with 60 g of lactose and 138 g of starch whereupon the mixture was wetted by a necessary amount of starch hydrogel Two grams of magnesium stearate were added to the mixture after it was granulated and homogenized.

The mixture was then pressed to tablets. Each tablet was about 250 mg weight and 5 mm diameter and contained a 10 mg dose of the active substance.

EXAMPLE 3

Antidiarrheal in suspension form:

500 mg of substance were dissolved in 20 ml of distilled water and homogenized together with the suspension prepared from 20 mg of colloidal silicon dioxide. The resulting suspension contained 10 mg of active substance in 5 ml.

It should be understood that while the specific compositions described herein illustrate preferred embodiments of the invention, various modifications and alterations can be made without departing from the spirit and scope thereof and that all said modifications which fall within the scope of the appended claims are intended to be included herein.

Apart from the antidiarrheal effect, the active substance possesses significant spasmolytic, antiulcerose and gastric cytoprotective effects.

What is claimed is:

1. A method of treating a host suffering from diarrhea consisting of administering to said host an effective amount of an anti-diarrheal composition in unit dosage form consisting of (±)-trans-2-(1-pyrrolidinyl) cyclohexylester of 3-(n)- pentyloxycarbanilic acid, or a salt of said ester with an acid selected from the group consisting of hydrochloric, adipic and fumaric acids as the effective agent and a pharmaceutically acceptable carrier selected from the group consisting of lactose, starch, starch hydrogel, colloidal silicon dioxide, magnesium stearate and mixtures thereof.

2. The method of claim 1 wherein said composition is administered in doses of b 10 and 20 mg per day for one to three days to a host having an average weight of 40 kg.

3. The method of claim 1 comprising administering for 2 to 3 days in a 10 mg daily dose.

4. The method of claim 1 wherein 20 mg of said composition is given for 3 days.

* * * * *